United States Patent [19]

Thuillier, born Nachmias et al.

[11] 4,188,388
[45] Feb. 12, 1980

[54] PHENOXY PYRIDAZINONES AND ANOREXIGENIC USE THEREOF

[75] Inventors: Germaine Thuillier, born Nachmias, Paris; Sylviane S. J. Mignonac, born Mondon, Chilly-Mazarin, both of France

[73] Assignee: Albert Rolland S.A., Paris, France

[21] Appl. No.: 898,988

[22] Filed: Apr. 21, 1978

[30] Foreign Application Priority Data

Apr. 28, 1977 [FR] France .............................. 77 12888

[51] Int. Cl.² .................... A61K 31/50; C07D 237/16
[52] U.S. Cl. ....................................... 424/250; 544/240
[58] Field of Search .............................. 544/240; 424/250

[56] References Cited

U.S. PATENT DOCUMENTS 3,671,525  6/1972  Reicheneder et al. ................. 71/92

OTHER PUBLICATIONS

Kamiya et al., Chem. Abs. 67, 3049s (1966).
Ueda et al., Chem. Abs. 69, 19332f (1967).
Unio et al., Chem. Abs. 71, 112960k (1969).
Ohgo et al., Chem. Abs. 76, 81138v (1970).
Jojima et al., Chem. Abs. 81, 120558g (1974).

Primary Examiner—Mark L. Berch
Attorney, Agent, or Firm—Stevens, Davis, Miller & Mosher

[57] ABSTRACT

Compounds of the formula I

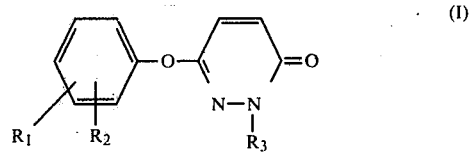

in which $R_1$ and $R_2$ each represent a hydrogen atom, a halogen atom, an alkyl group containing 1 to 3 carbon atoms, an alkoxy group containing 1 to 3 carbon atoms or a trifluoromethyl group; and $R_3$ represents an alkyl group containing 1 to 4 carbon atoms mono- or polyhydroxyl substituted, the alcohol functions being unesterified or esterified by benzoic acid are useful as in therapy as medicaments, in particular as psychotropic and anorexigenic agents.

18 Claims, No Drawings

PHENOXY PYRIDAZINONES AND ANOREXIGENIC USE THEREOF

The present invention relates to 3-pyridazinone derivatives, their preparation and their use in therapy as medicaments, in particular as psychotropic and anorexigenic agents.

According to the invention, there are provided compounds of the formula I:

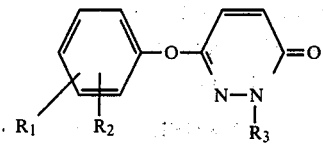

in which
each of $R_1$ and $R_2$, which may be the same or different, represents a hydrogen atom, a halogen atom, an alkyl group containing 1 to 3 carbon atoms, an alkoxy group containing 1 to 3 carbon atoms or a trifluoromethyl group; and
$R_3$ represents an alkyl group containing 1 to 4 carbon atoms which is mono- or poly-hydroxyl substituted (suitably mono- or dihydroxyl substituted), the alcohol functions being unesterified or esterified by an unsubstituted or substituted benzoic acid. The invention also provides compounds which in the metabolic system liberate the compounds of the formula I.

In the formula I $R_1$ preferably represents a hydrogen atom and $R_2$ is preferably in the 4-position and represents a halogen atom, especially a chlorine atom.

$R_3$ suitably represents a mono- or di-hydroxyalkyl group containing 1 to 4 carbon atoms, the alcohol functions being unesterified or esterified by a benzoic acid which is unsubstituted or substituted by halogen, alkyl or alkoxy. Preferably the alcohol functions of $R_3$ are free from esterification.

According to the invention, there are particularly provided compounds of the formula I in which $R_1$ represents a hydrogen atom, $R_2$ represents a chlorine or fluorine atom or a methyl or trifluoro-methyl group, and $R_3$ represents a hydroxyalkyl, benzoyloxyalkyl, or p-chloro-, p-methyl- or p-methoxybenzoyloxyalkyl group or a dihydroxyalkyl group.

The compounds of the formula I may be prepared by replacement of the hydrogen atom in the 2-position on the 3-pyridazinone group of compounds of the formula II

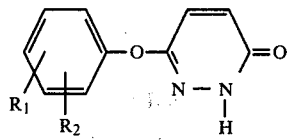

in which $R_1$ and $R_2$ have the same meanings as above, e.g. by reaction in basic medium, with a halogenated aliphatic alcohol of the formula $R_3X$ (in which $R_3$ has the same meaning as above and X represents a halogen atom); in neutral or basic medium with an epoxide having 2 to 4 carbon atoms; with formaldehyde when $R_3$ contains a single carbon atom; or in basic medium with a halogenated aliphatic ketone, the ketone so obtained being then catalytically or chemically reduced to give an alcohol of the formula I.

When a halogenated aliphatic mono- or polyhydric alcohol is used all $R_3$ groups can be obtained. When an epoxide is used the $R_3$ group obtained is monohydroxylated on the β-carbon atom and it is possible to obtain by this way a dihydroxylated $R_3$ group by using e.g. glycidol. When formaldehyde is used $R_3$ is a hydroxymethyl group and when a halogenated aliphatic ketone is used $R_3$ in the product (after reduction) represents a monohydroxylated alkyl group containing 3 or 4 carbon atoms.

The compounds of the formula I may also advantageously be prepared by reaction, in the presence of a base, of a phenol of the formula III

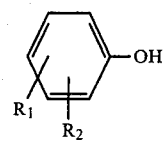

with a 6-chloro-3-pyridazinone of the formula IV

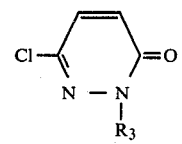

in which formulae $R_1$, $R_2$ and $R_3$ have the same meanings as above.

The 6-phenoxy-2-hydroxyalkyl-3-pyridazinones of the formula I may, if desired, be esterified by reaction with an unsubstituted or substituted benzoic acid or derivative thereof such as a benzoic acid chloride, anhydride or ester.

The 6-phenoxy-3-pyridazinones of the formula II may be prepared by reaction of a phenol of the formula III with 3,6-dichloro-pyridazine, in the presence of a base, to give the 3-phenoxy-6-chloro-pyridazines, which are hydrolysed in acid medium, for example in acetic acid.

The following Examples illustrate the invention. The melting points mentioned have been measured in a capilliary tube.

EXAMPLE 1

2-(2-Hydroxyethyl)-6-(4-chlorophenoxy)-3-pyridazinone

Method 1 a. 68.6 g (0.7 mole) maleic acid anhydride are introduced rapidly into a solution at 100° C. of 75.6 g (0.7 mole) hydrazine dihydrochloride in 500 ml water. After 3 hours at this temperature, the solution is left to return to ambient temperature and then the precipitate of 3,6-dihydroxy-pyridazine filtered.

Yield=85% - M.Pt.=300° C.

b. 35 g of 3,6-dihydroxy-pyridazine and 300 ml phosphorus oxychloride are maintained at reflux temperature for 5 hours. After removal of the volatile fractions by distillation under reduced pressure, the residual solid is deposited onto 500 g crushed ice; the mixture is neutralised by addition of ammonia solution and the precipitate which appears isolated. 29 g of 3,6-dichloro-pyridazine, recrystallisable from cyclohexane, are thus obtained.

M.Pt.=68°-9° C.

c. A mixture of 14.9 g 3,6-dichloro-pyridazine, 10.45 g 4-chlorophenol and 13.8 g potassium carbonate is maintained for half an hour at 160° C., and then poured into an aqueous dilute sodium hydroxide solution. The precipitate which appears in isolated and recrystallised from an aromatic solvent. There is thus obtained, at 70% yield, 3-chloro-6-(4-chlorophenoxy)-pyridazine which melts at 119° C.

d. A solution of 10 g 3-chloro-6-(4-chlorophenoxy)-pyridazine in 100 ml acetic acid is maintained at reflux temperature for a few hours. The precipitate which appears on cooling is isolated and then recrystallised from butanol. There is thus obtained, at 80% yield, 6-(4-chlorophenoxy)-3-pyridazinone which melts at 202° C.

e. 6 g potassium hydroxide are dissolved in 60 ml methanol and then 22 g 6-(4-chlorophenoxy)-3-pyridazinone and the mixture maintained at the reflux temperature of the solvent for 30 minutes. There are then added, little by little with stirring, without application of heat, 10 g 2-chloroethanol and then the mixture is maintained at reflux temperature for about 5 hours. The potassium chloride formed is removed by hot filtration; the final product precipitates from the solution at 5° C.

Yield=80%—M.Pt.=142°-5° C. (recrystallisation from CH₃OH).

This last reaction may be effected with 90% yield in dimethylformamide, in the presence of potassium hydroxide or carbonate, for example:

5 g 6-(4-chlorophenoxy)-3-pyridazinone and 6.5 g potassium carbonate are dissolved in 100 ml dimethylformamide. After heating for 1 hour, 3 g 2-chloroethanol are introduced and the mixture maintained for a few hours under reflux. The solvent is removed under reduced pressure and there are obtained 5.3 g of the final product, which precipitates from water.

Method 2

A. 6 g 3,6-dichloro-pyridazine in 50 ml acetic acid are maintained under reflux for 4 hours. The solvent is removed under reduced pressure and the product recrystallised from benzene to give 5 g 6-chloro-3-pyridazinone melting at 141° C.

B. 4 g of the product obtained according to A and 6 g potassium carbonate are dissolved in 50 ml dimethylformamide. 3 g 2-chloroethanol are poured into the medium and the mixture maintained at a temperature of about 70° C. for 2 hours. The solvent is then distilled and the residue recrystallised from benzene to give 4 g of product melting at 102° C.

C. 5 g 4-chlorophenol are dissolved in 50 ml butanol into which has been introduced 1 g sodium. After half an hour at 100° C., 6.5 g 2-(2-hydroxyethyl)-6-chloro-3-pyridazinone are introduced and the mixture maintained at its reflux temperature for several hours. The mixture is cooled, neutralised, the solvent is removed under reduced pressure and then the remaining starting materials are removed in aqueous alkali and neutral solutions.

There are obtained, at 50% yield, 6.8 g 2-(2-hydroxyethyl)-6-(4-chlorophenoxy)-3-pyridazinone.

This reaction may also be carried out in other solvents such as dimethoxyethane or dimethylformamide and operating at about 100° C., the phenolate being prepared by action of sodium hydride, alkali alcoholate, alkali carbonate or hydroxide. This reaction can also be carried out without solvent in the presence of potassium carbonate at about 150° C.

EXAMPLE 2

2-(2-Hydroxyethyl)-6-(2-chlorophenoxy)-3-pyridazinone

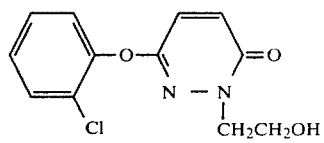

2.4 g sodium are dissolved in 100 ml anhydrous 1-butanol and then 30 g 6-(2-chlorophenoxy)-3-pyridazinone prepared in a manner analogous to Example 1 (M.Pt=182° C.) and the reaction mixture is maintained at 100° C. for 1 hour. 9 g 2-chloroethanol are then introduced without application of heat and then the mixture maintained for 9 hours at reflux temperature. The solvent is removed under reduced pressure, 50 ml aqueous N-sodium hydroxide solution are poured onto the residue and the final product is extracted in diethyl ether.

Yield=40%—M.Pt=78°-79° C. (diethyl ether/petroleum ether).

EXAMPLE 3

2-(2-Hydroxypropyl)-6-(4-chlorophenoxy)-3-pyridazinone

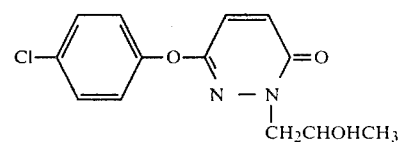

Method 1

A suspension of 11 g 6-(4-chlorophenoxy)-3-pyridazinone in anhydrous ethanol, in the presence of a large excess of propylene oxide (8 to 9 g), is maintained under reflux for 24 hours. After total dissolution, the solvent is removed under reduced pressure; the residual oil is crystallised from diethyl ether.

Yield=70%—M.Pt=97°-98° C. (n-butyl ether).

Method 2

A. Preparation of 2-oxopropyl-6-(4-chlorophenoxy)-3-pyridazinone

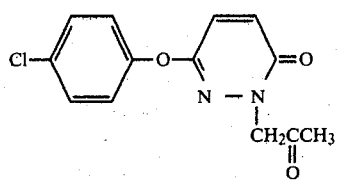

10 g 6-(4-chlorophenoxy)-3-pyridazinone are introduced into a solution of 3 g potassium hydroxide in 45 ml methanol and the mixture refluxed for 30 minutes before adding 4.6 g chloroacetone. After refluxing for 15 hours, the potassium salt is removed by filtration and then the solvent under reduced pressure. 50 ml aqueous N-sodium hydroxide solution is poured onto the residue and then the final product extracted in chloroform.

Yield=40%—M.Pt=120° C. (isopropyl ether).

B. Reduction 2.7 g of the product obtained above are suspended in 50 ml methanol. 0.2 g Sodium borohydride is introduced little by little. After 30 minutes' stirring, 50 ml aqueous 2 N-sodium hydroxide solution are added, the methanol is evaporated and the final product is extracted in chloroform.

Yield=30%.

EXAMPLE 4

2-Hydroxymethyl-6-(4-chlorophenoxy)-3-pyridazinone

Into a solution, at reflux, of 7 g 6-(4-chlorophenoxy)-3-pyridazinone in 100 ml ethanol, there are poured 30 ml of a 20% aqueous formaldehyde solution, and then after 1 hour a further 30 ml. After refluxing for 3 hours, the solution is concentrated to half, and 100 ml water are introduced into the mixture from which 4.5 g of final product are extracted in chloroform. After recrystallisation from benzene, the product melts at 162° C. (with decomposition)

EXAMPLE 5

2-[2'-(4-Chlorobenzoyloxy)-ethyl]-6-(4-chlorophenoxy)-3-pyridazinone

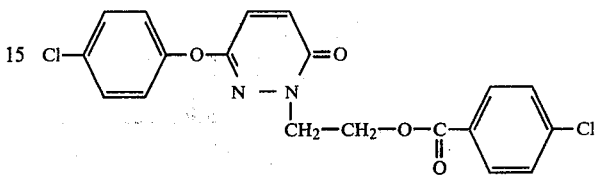

4 g 4-Chlorobenzoyl chloride are added, bit by bit, to 100 ml of a solution of 5.3 g 2-(2-hydroxethyl)-6-(4-chlorophenoxy)-3-pyridazinone and 2.5 g triethylamine in chloroform. After 5 to 6 hours under reflux, the solution is washed with aqueous sodium bicarbonate solution, aqueous dilute hydrochloric acid solution and then water. After drying and removal of the solvent, the residue is recrystallised from isopropyl ether to give the pure final product.

Yield=55%—M.Pt.=109° to 10° C.

The compounds of the following Examples have been prepared by applying one of the operational methods described in Examples 1 to 5 with equivalent yields.

| Example No. | $R_1$ | $R_2$ | $R_3$ | M.Pt (°C.) | M.Pt (°C.) of unsubstituted (R₃=H) |
|---|---|---|---|---|---|
| 6 | 4-Cl | H | $CH_2CHOHCH_2OH$ | 98–98.5 | 202 |
| 7 | 4-Cl | H | $CH_2CH_2CH_2OH$ | 77–78 | 202 |
| 8 | 4-Cl | H | $CH_2C(CH_3)_2OH$ | 109–110 | 202 |
| 9 | 2-$CH_3$ | H | $CH_2CH_2OH$ | 68–69 | 170 |
| 10 | 4-F | H | $CH_2CH_2OH$ | 116–117 | 165 |
| 11 | 4-$CH_3$ | H | $CH_2CH_2OH$ | 122–123 | 170 |
| 12 | 3-$CF_3$ | H | $CH_2CH_2OH$ | 111–112 | 131 |
| 13 | 4-Cl | H | $CH_2CHOHCH_2CH_3$ | 97–98 | 202 |
| 14 | 4-Cl | H | $CH_2CH_2OCOC_6H_5$ | 104 | 202 |
| 15 | 4-Cl | H | $CH_2CH_2OCO$-C₆H₄-$CH_3$ | 108 | 202 |
| 16 | 4-Cl | H | $CH_2CH_2OCO$-C₆H₄-$OCH_3$ | 90 | 202 |
| 17 | 3-Cl | H | $CH_2CH_2OH$ | 78 | 144 |
| 18 | 2-$C_2H_5O$ | H | $CH_2CH_2OH$ | 100 | 152 |
| 19 | 4-$CH_3O$ | H | $CH_2CH_2OH$ | 88 | 194 |

-continued $$\text{(structure: phenyl ring with } R_1, R_2 \text{ substituents)}-O-\text{(ring)}=O, \text{N}-\text{N}-R_3$$

| Example No. | $R_1$ | $R_2$ | $R_3$ | M.Pt (°C.) | M.Pt (°C.) of: (structure with $R_1, R_2$, N—N—H) |
|---|---|---|---|---|---|
| 20 | 4-Br | H | $CH_2CHOHCH_2OH$ | 102 | 191 |
| 21 | 2-$CH_3$ | 3-$CH_3$ | $CH_2CH_2OH$ | 122 | 212 |

Toxicological and pharmacological tests on animals have shown the low toxicity of the compounds, their anorexigenic properties and their psychotropic properties of analeptic type, associated sometimes with a valuable anxiolytic activity.

The oral $LD_{50}$s determined in the mouse and calculated according to a method described in Journal Pharmacol. Exp. Ther. 96 99-113 (1949) are all equal to or above 750 mg/kg.

The psychotropic activity of the compounds of the invention have been shown and their nature determined by different tests of which some are reported below.

Activity of psychoanaleptic type

This shown by an increase in the vigilance of the mice observed for example for the compound of Example 1 after oral administration of a dose corresponding to 10 mg/kg. Further, an increase in the mobility and exploration of the mice submitted to the "tube test" appears. The oral $ED_{50}$ of the compounds of Examples 1 and 3 are 50 mg/kg in these tests.

Activity of antidepressive type

A compound is considered to have an antidepressive activity when its administration reduces hypothermia in mice which have been injected intraperitoneally with 3 mg/kg reserpine; the compound of Example 1 acts when it is administered orally at 25 mg/kg and most of the compounds according to the invention have a minimum active dose in the region of 100 mg/kg.

Activity of anxiolytic type

This is shown by the "4 plates test" described in "Eur. J. Pharm. 4 145-51 (1968)". Certain of the compounds according to the invention, although not having distinct psychoanalytic activity at very low dose, are active in this test, such as the compounds of Examples 8 and 15 ($ED_{50}=50$ mg/kg) or 6 ($ED_{50}=75$ mg/kg). The determined $ED_{50}$s are in generaly below 100 mg/kg.

Anticholinergic activity

Like tricyclic psychostimulants and anti-depressives, the derivatives of the invention have an anticholinergic activity. In effect, their previous administration per os diminishes the tremblings in mice caused by intraperitoneal injection of 0.5 mg/kg oxotremorine. For example the $ED_{50}$ of the compound of Example 1 is 25 mg/kg and that of that of Example 3 is 40 mg/kg.

Anorexigenic activity

Anorexia in mice, provoked by oral administration of the compounds, has been estimated as a function of the quantity of nourishment taken by the animals during the hour following administration of the test compound. The compound of Example 1 has an $ED_{50}$ in the region of 30 mg/kg; the compounds of Examples 2, 3, 8 and 15 have $ED_{50}$s below 75 mg/kg.

The compounds of formula I, having a psychotropic activity of analeptic and anxiolytic type, may, according to the invention, be used as active principle in medicaments administrated in the treatment of certain nervous maladies. Their anorexigenic activity permits their use also as medicaments to the treatment of overweight due to diverse causes.

Accordingly the invention also provides a pharmaceutical composition which contains, as active principle, a compound of the formula I together with a pharmaceutically acceptable excipient.

The invention also provides a method of treatment of a patient which method comprises administering to the patient a compound of the formula I.

The compounds of the formula I may be administered orally, in the form of tablets or capsules, rectally or parenterally associated with pharmaceutically acceptable excipients and at unitary doses comprising between 10 and 200 mg.

For example, tablets containing 100 mg of active principle may be prepared by compression of a mixture of 100 mg of the compound described in Example 1 with 250 mg of microcrystalline cellulose.

We claim:

1. A compound of the formula $$\text{(phenyl ring with } R_1, R_2)-O-\text{(ring)}=O, \text{N}-\text{N}-R_3$$

wherein
each of $R_1$ and $R_2$ is independently selected from the group consisting of hydrogen, halogen, $C_{1-3}$ alkyl, $C_{1-3}$ alkoxy and trifluoromethyl;
$R_3$ is —($C_{1-4}$ alkyl)—$OR_4$ or

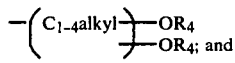

R$_4$ is hydrogen, benzoyl, (C$_{1-4}$ alkyl)-benzoyl, halobenzoyl or (C$_{1-4}$ alkoxy)-benzoyl.

2. A compound according to claim 1 in which R$_1$ represents a hydrogen atom and R$_2$ is in the 4-position and represents a halogen atom.
3. A compound of claim 1 wherein R$_4$ is hydrogen.
4. A compound of claim 1 wherein R$_1$ is hydrogen.
5. A compound of claim 4 wherein R$_2$ is chlorine, fluorine, methyl or trifluoromethyl.
6. A compound according to claim 1 which is 2-(2-hydroxyethyl)-6-(4-chlorophenoxy)-3-pyridazinone.
7. A compound according to claim 1 which is 2-(2,3-dihydroxypropyl)-6-(4-chlorophenoxy)-3-pyridazinone.
8. A compound according to claim 1 which is 2-(2-hydroxypropyl)-6-(4-chlorophenoxy)-3-pyridazinone.
9. A compound of claim 5 wherein R$_3$ is hydroxy (C$_{1-4}$ alkyl), benzoyloxy (C$_{1-4}$ alkyl), p-chlorobenzoyloxy (C$_{1-4}$ alkyl), p-methylbenzoyloxy (C$_{1-4}$ alkyl), p-methoxybenzoyl (C$_{1-4}$ alkyl) or dihydroxy (C$_{1-4}$ alkyl).
10. A pharmaceutical composition suitable for treating an overweight patient which comprises an amount effective for providing an anorexigenic effect to said patient of a compound of the formula

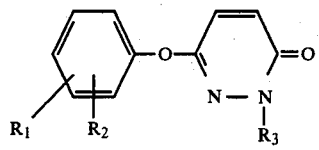

wherein
each of R$_1$ and R$_2$ is independently selected from the group consisting of hydrogen, halogen, C$_{1-3}$ alkyl, C$_{1-3}$ alkoxy and trifluoromethyl;
R$_3$ is —(C$_{1-4}$ alkyl)—OR$_4$ or

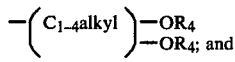

R$_4$ is hydrogen, benzoyl, (C$_{1-4}$ alkyl)-benzoyl, halobenzoyl or (C$_{1-4}$ alkoxy)-benzoyl;
and a pharmaceutically acceptable carrier for said compound.

11. A method of treating a patient susceptible to being overweight which comprises administering to said patient an anorexigenically effective amount of a compound of the formula:

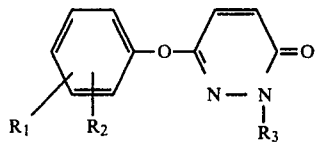

wherein
each of R$_1$ and R$_2$ is independently selected from the group consisting of hydrogen, halogen, C$_{1-3}$alkyl, C$_{1-3}$alkoxy and trifluoromethyl;
R$_3$ is —(C$_{1-4}$alkyl)—OR$_4$ or

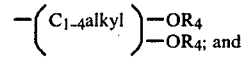

R$_4$ is hydrogen, benzoyl, (C$_{1-4}$alkyl)-benzoyl, halobenzoyl or (C$_{1-4}$alkoxy)-benzoyl
and a pharmaceutically acceptable carrier therefor.

12. A method of claim 11, wherein said compound is administered orally or parenterally.
13. A method of claim 12, wherein said compound is administered orally.
14. A method of providing a patient with a psychoanaleptic effect which comprises administering to a patient a psychoanaleptically effective amount of a compound of the formula:

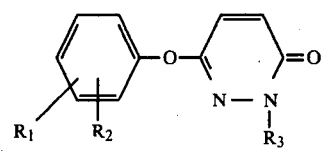

wherein
each of R$_1$ and R$_2$ is independently selected from the group consisting of hydrogen, halogen, C$_{1-3}$alkyl, C$_{1-3}$alkoxy and trifluoromethyl;
R$_3$ is —(C$_{1-4}$alkyl)—OR$_4$ or

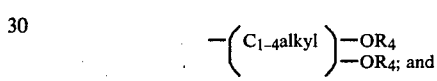

R$_4$ is hydrogen, benzoyl, (C$_{1-4}$alkyl)-benzoyl, halobenzoyl or (C$_{1-4}$alkoxy)-benzoyl
and a pharmaceutically acceptable carrier therefor.

15. A method of claim 14, wherein said compound is administered orally or parenterally.
16. A method of claim 15, wherein said compound is administered orally.
17. A method of claim 14 wherein said compound is administered at a unit dosage of from 10 to 200 mg.
18. A pharmaceutical composition suitable for treating a patient requiring a psychoanaleptic effect which comprises an amount effective for providing said psychoanaleptic effect to said patient of a compound of the formula:

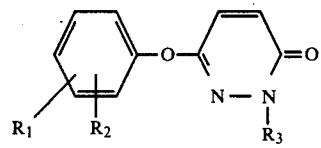

wherein
each of R$_1$ and R$_2$ is independently selected from the group consisting of hydrogen, halogen, C$_{1-3}$alkyl, C$_{1-3}$alkoxy and trifluoromethyl;
R$_3$ is —(C$_{1-4}$alkyl)—OR$_4$ or

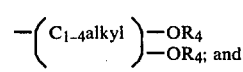

R$_4$ is hydrogen, benzoyl, (C$_{1-4}$alkyl)-benzoyl, halobenzoyl or (C$_{1-4}$alkoxy)-benzoyl;
and a pharmaceutically acceptable carrier for said compound.

* * * * *